(12) United States Patent  (10) Patent No.: US 6,719,560 B2
Capt  (45) Date of Patent: Apr. 13, 2004

(54) RACK FOR DENTAL BURRS

(75) Inventor: Michel Capt, Vallorbe (CH)

(73) Assignee: Maillefer Instruments Holding SA, Ballaigues (CH)

( * ) Notice: Subject to any disclaimer, the term of this patent is extended or adjusted under 35 U.S.C. 154(b) by 93 days.

(21) Appl. No.: 09/998,300

(22) Filed: Dec. 3, 2001

(65) Prior Publication Data

US 2002/0068255 A1 Jun. 6, 2002

(30) Foreign Application Priority Data

Dec. 1, 2000 (EP) .............................................. 00126234

(51) Int. Cl.⁷ ................................................. A61C 13/38
(52) U.S. Cl. ........................ 433/77; 206/369; 206/379; 211/69
(58) Field of Search ........................... 433/77, 165, 166; 206/368, 369, 370, 379; 211/69

(56) References Cited

U.S. PATENT DOCUMENTS

| 1,446,921 | A | * | 2/1923 | Montag | 206/369 |
| 4,253,830 | A | * | 3/1981 | Kazen | 433/77 |
| 4,306,862 | A |   | 12/1981 | Knox | 433/77 |
| 5,108,287 | A | * | 4/1992 | Yee et al. | 433/77 |
| 5,312,250 | A | * | 5/1994 | Ellman et al. | 433/77 |
| 5,358,112 | A |   | 10/1994 | Gardner | 206/369 |
| 5,589,137 | A | * | 12/1996 | Markin et al. | 422/104 |
| 5,878,882 | A | * | 3/1999 | Kohagura | 206/379 |
| 6,328,565 | B1 | * | 12/2001 | Rose | 433/77 |
| 6,349,827 | B1 | * | 2/2002 | Feder | 211/69 |

* cited by examiner

Primary Examiner—John J. Wilson
(74) Attorney, Agent, or Firm—Young & Thompson

(57) ABSTRACT

The rack for dental burrs includes a base (1) and a cover (5) and is provided with a plurality of passages (8) distributed over its surface, each adapted to receive a dental burr. Each of these passages (8) includes at least two piercings (9, 10) of different diameters corresponding to standard diameters of shanks of dental burrs.

11 Claims, 3 Drawing Sheets

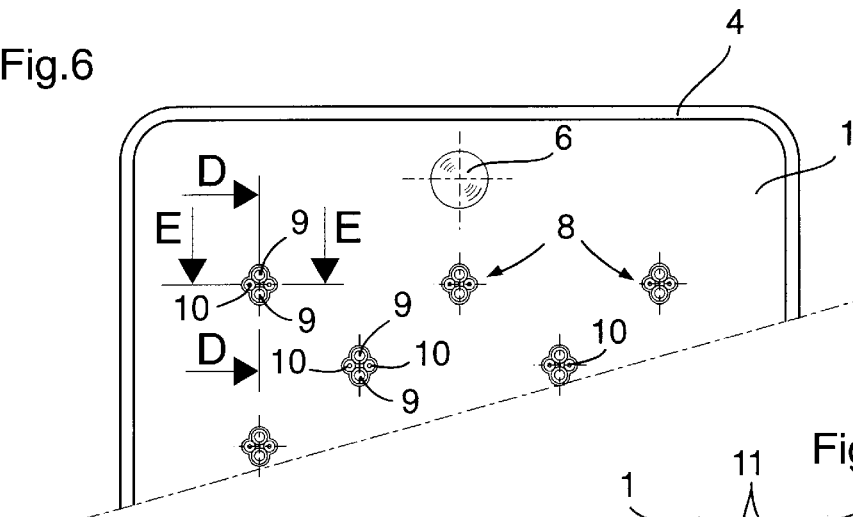
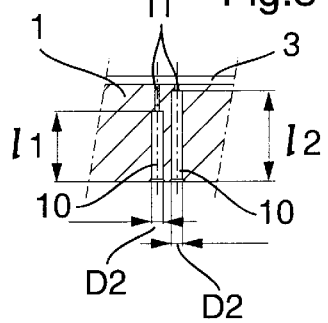
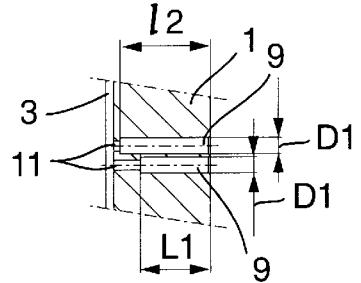
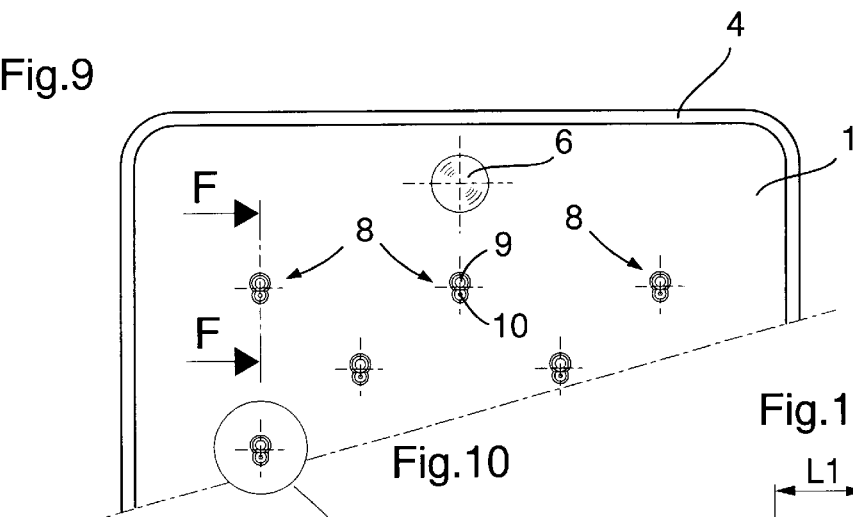
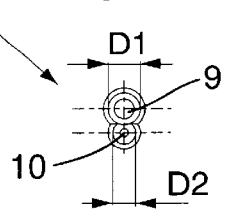
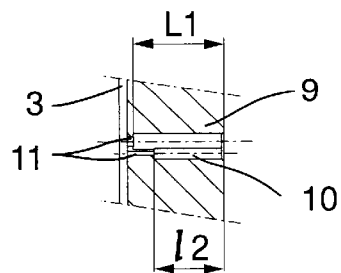

RACK FOR DENTAL BURRS

BACKGROUND OF THE INVENTION

The present invention relates to racks for dental burrs. Producers of dental burrs have the custom among other things of selling sets of dental burrs including all the burrs necessary for a certain operation on a same support or rack. Thus, the dentist can select a rack as a function of the operation he will perform and thus has at hand all the burrs necessary for this operation. Such racks comprise a base provided with passages whose diameter and depth correspond to each burr to be used. Moreover, the succession of these passages corresponds to the succession of the burrs in the order in which they are used by the dentist for the operation in question. These racks also comprise a cover and the whole is arranged so as to be washed and sterilized in a single operation, the rack being full of burrs.

These standard racks, provided with a predetermined set of burrs, do not entirely satisfy dentists. Thus, each dentist has a personal practice and each operation is particular and depends particularly on the dental characteristics of the patient. Thus, it frequently happens that such standard sets of burrs comprise too many or too few burrs or burrs unsuitable for the dentist's practice. This can lead to loss of time, discarding unused burrs and the augmentation of the set by burrs selected by the dentist.

With the use of such standard racks, it rarely happens that the set of burrs can be used in the intended sequence without any change such that the use of these standard racks is very limited.

SUMMARY OF THE INVENTION

The present invention has for its object the provision of a rack that can accept in the order desired by the dentist, the set of burrs necessary for an operation, comprising burrs which the dentist will himself have selected and placed in the order he wishes so as to facilitate the work of the dentist.

The present invention has for its object a rack for dental burrs overcoming the mentioned drawbacks and permitting carrying out the objects recited above.

BRIEF DESCRIPTION OF THE DRAWINGS

The accompanying drawings show schematically and by way of example three particular embodiments of the rack for dental burrs, according to the invention.

FIG. 6 is a fragmentary plan view of the base of a second embodiment of the rack.

FIGS. 7 and 8 are cross-sectional views on the lines DD and E—E of FIG. 6.

FIG. 9 is a fragmentary perspective view of the base of a third embodiment of the rack.

FIG. 10 is an enlarged view of a portion of the surface of the base shown in FIG. 9.

FIG. 11 is a cross-sectional view on the line F—F of FIG. 9.

DETAILED DESCRIPTION OF THE INVENTION

Figure 1A:
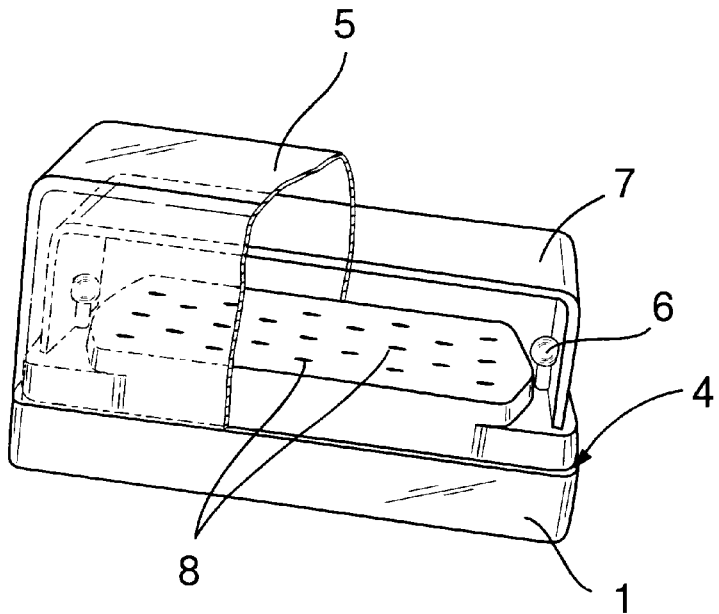
FIG. 1a shows the complete rack in perspective.
Figure 1B:
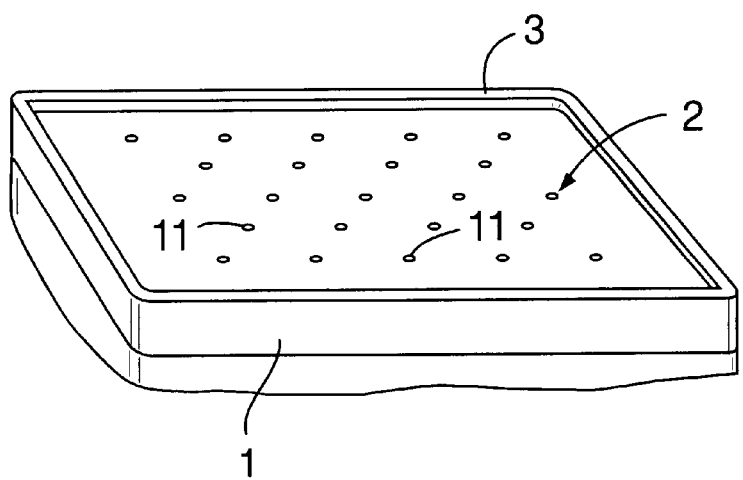
FIG. 1b is a fragmentary perspective view from below, of the rack.

The rack for dental burrs shown in FIGS. 1a and 1b comprises a base 1 of synthetic resin resistant to washing and sterilization. This base 1 comprises on its lower surface a recess 2 surrounded by a flange 3. The periphery of this base 1 comprises a shoulder 4 serving to support on the base a cover 5 also of synthetic resin, but preferably transparent or translucent and resistant to washing and sterilization.

The upper surface of the base 1 comprises two securement members 6 serving to secure removably on this base a protective U-shaped sheet 7.

The base 1 is pierced through by a plurality of through passages 8 disposed regularly about the surface of the base. As will be seen later in detail, these passages 8 are adapted to receive the shank of a dental burr. The passages are separated by a sufficient distance for a dentist to select the burrs in the order in which they are used by the dentist for a predetermined operation.

In the illustrated example, the securement members 6 of the protective sheet 7 as well as this latter, are made of stainless steel, and thus all the constituent elements of the rack can undergo, without alteration, washing, cleaning and sterilization.

The protective sheet 7 serves to hold in place dental burrs disposed in the passages 8 during the operations of washing and sterilization carried out with the cover not mounted on the support, to prevent the burrs from separating from the base 1.

In the first embodiment of the rack shown in FIGS. 2 to 5, each through passage 8 of the base 1 comprises six recesses, three recesses 9 of large diameter D1, 2.35 mm, and three recesses 10 of small diameter D2, 1.60 mm, which diameters correspond to the standard ISO diameter of the shanks of dental burrs. There can thus be disposed in each passage 8 as desired a dental burr whose shank has a large standard diameter or a small standard diameter.

Moreover, the three piercings of large diameter 9 of a same passage 8 have different lengths or depths L1, L2, L3. Finally, the three piercings of small diameter 10 of a same passage 8 have different lengths or depths 11, 12, 13.

The standard ISO burrs having shanks of different length according to their shape and size can thus all be disposed in a recess corresponding to them, in each passage 8.

In this way, the dentist selects the dental burrs, no matter what the diameter and length of their shank, from among the standard ISO burrs at his disposal, which are needed by him for a predetermined operation or work. He then places them in the order of use, each in one of the piercings of a passage 8 and can thus establish a particularized set of dental burrs adapted to his manner of working for a given operation.

Once the burrs are in place, the protective sheet is emplaced, fixed on the securement member 6, and the open rack as well as its cover can then be washed and sterilized. After sterilization, the cover 5 is placed on the base 1 and the rack is stored until use of the burrs by the dentist.

In the second embodiment shown in FIGS. 6 to 8, the passages 8 are constituted of only four piercings each, two piercings 9 of large diameter D1 and of different lengths L1, L2 and two piercings of small diameter D2 and also of different length 11, 12.

Figure 2:
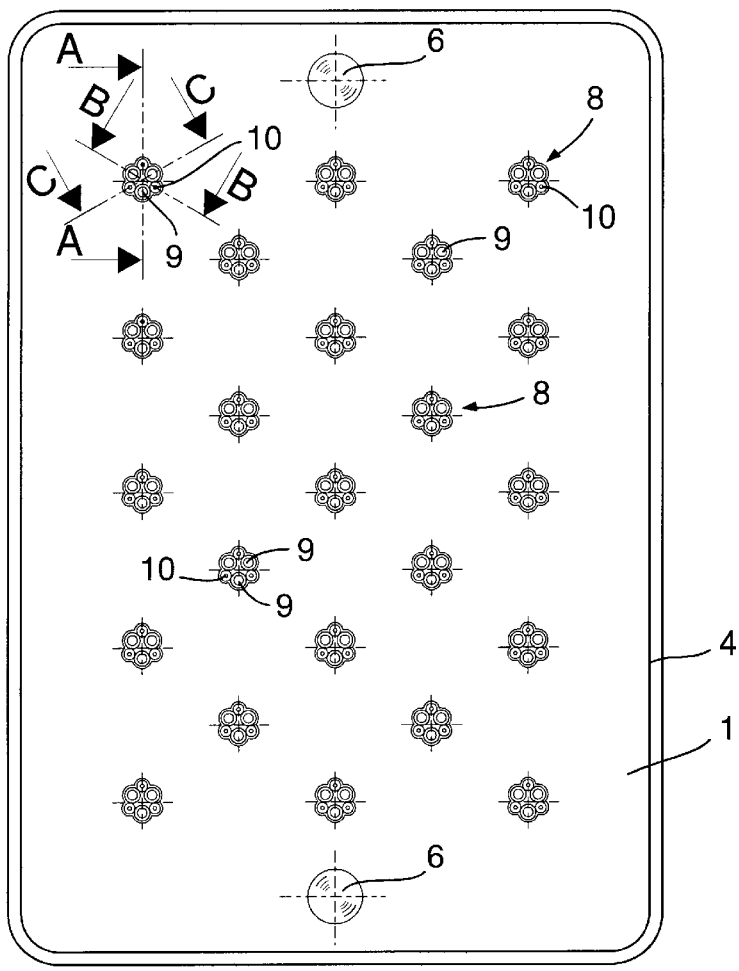
FIG. 2 is a plan view of the base of a first embodiment of the rack.
Figure 3:
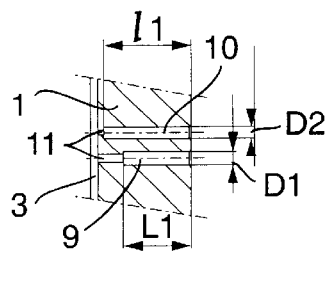
FIGS. 3,4 and 5 are cross-sectional views on the lines A—A-; B—B and C—C of FIG. 2.
Figure 4:
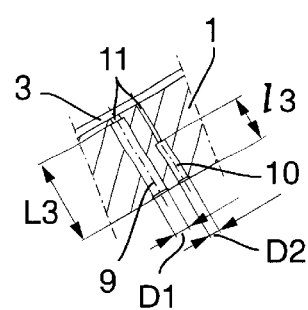
Figure 5:
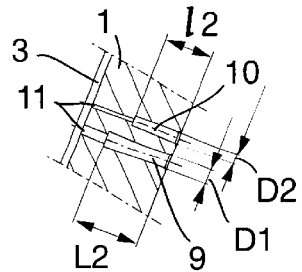

In the first two embodiments, as seen in FIGS. 2 and 6, the piercings of each passage are juxtaposed, such that a circumference of one piercing touches the circumference of an adjacent piercing.

In the third embodiment shown in FIGS. 9 and 11, the passages 8 are constituted by two overlapping piercings, one piercing 9 of large diameter D1 and length L1, and the other of small diameter D2 and of a length 12.

In all the embodiments, at least one of the piercings 9, 10 of each passage 8 through the base 1 is prolonged by a piercing of smaller diameter 11 to establish communication between the lower surface and the upper surface of the support, permitting better washing and better sterilization of the bases and particularly of the passages 8.

The interest of this new rack for dental burrs is that each dentist can insert therein, in the order he wishes, no matter what standard burr in the passages 8, which always have a diameter and a depth suitable for the selected burr.

Of course, these polyvalent racks can be sold empty, the dentist then supplying them with burrs according to his needs, or be provided with a quite precise sequence of burrs which would then be indicated on the rack to identify it.

These new racks are less costly than those existing at present, because they are mass produced, they resist sterilization, and permit an infinite combination of different sequences of burrs. As a result, the dentist need have fewer burrs, and less risk of manipulation and confusion by the practitioner who himself prepares the sequences of burrs.

What is claimed is:

1. Rack for dental burs, comprising a base having an upper surface and a lower surface, and a cover;

said base having a plurality of separate passages distributed over its upper surface;

said separate passages being separated by a sufficient distance for a dentist to select the burs in the order in which they are used by the dentist;

each passage adapted to receive a dental bur, and comprising at least two juxtaposed piercings of different diameters corresponding to standard diameters of dental bur shafts, such that a circumference of one piercing touches the circumference of an adjacent piercing.

2. The rack according to claim 1, wherein the piercings of a passage have different depths corresponding to lengths of standard shanks of dental burs.

3. The rack according to claim 1, wherein each passage comprises four adjacent piercings, two piercings of a large diameter and two piercings of a small diameter, and the depth of the two piercings of large diameter is different, as is the length of the two piercings of small diameter.

4. The rack according to claim 1, wherein each passage comprises six adjacent piercings, three piercings of a large diameter and three piercings of a small diameter.

5. The rack according to claim 4, wherein the piercings of the same diameter of a passage have different depths.

6. The rack according to claim 1, wherein each passage comprises at least one piercing connected to the lower surface of the base by a piercing of a smaller diameter than that of the corresponding piercing.

7. The rack according to claim 1, wherein the upper surface of the base comprises securement members for a protective sheet, said sheet being adapted to be secured removably to the base via said securement members.

8. Rack for dental burs, comprising a base having an upper surface and a lower surface, and a cover;

said base having a plurality of separate passages distributed over its upper surface;

said separate passages being separated by a sufficient distance for a dentist to select the burs in the order in which they are used by the dentist;

each passage adapted to receive a dental bur, and comprising at least two overlapping piercings of different diameters corresponding to standard diameters of dental bur shafts.

9. The rack according to claim 8, wherein the piercings of a passage have different depths corresponding to lengths of standard shanks of dental burs.

10. The rack according to claim 8, wherein each passage comprises at least one piercing connected to the lower surface of the base by a piercing of a smaller diameter than that of the corresponding piercing.

11. The rack according to claim 8, wherein the upper surface of the base comprises securement members for a protective sheet, said sheet being adapted to be secured removably to the base via said securement members.

* * * * *